(12) United States Patent
Guidotti et al.

(10) Patent No.: US 7,465,688 B2
(45) Date of Patent: Dec. 16, 2008

(54) PROCESS FOR THE ISOMERIZATION OF METALLOCENE COMPOUNDS

(75) Inventors: Simona Guidotti, Malalbergo-Bologna (IT); Davide Balboni, Ferrara (IT)

(73) Assignee: Basell Polyolefine GmbH, Wesseling (DE)

( * ) Notice: Subject to any disclaimer, the term of this patent is extended or adjusted under 35 U.S.C. 154(b) by 132 days.

(21) Appl. No.: 10/573,750

(22) PCT Filed: Sep. 7, 2004

(86) PCT No.: PCT/EP2004/010020

§ 371 (c)(1),
(2), (4) Date: Mar. 29, 2006

(87) PCT Pub. No.: WO2005/030783

PCT Pub. Date: Apr. 7, 2005

(65) Prior Publication Data

US 2007/0060728 A1    Mar. 15, 2007

Related U.S. Application Data

(60) Provisional application No. 60/509,892, filed on Oct. 9, 2003.

(30) Foreign Application Priority Data

Sep. 29, 2003  (EP)  .................................. 03103599

(51) Int. Cl.
*B01J 31/18*  (2006.01)
(52) U.S. Cl. ....................... 502/164; 502/124; 502/123; 502/152; 502/167; 526/160; 526/170; 526/943; 556/52; 556/53

(58) Field of Classification Search ................. 526/160, 526/943, 170; 502/124, 123, 152, 164, 167; 556/53, 52; 586/52
See application file for complete search history.

(56) References Cited

U.S. PATENT DOCUMENTS

| 5,830,821 A | 11/1998 | Rohrmann et al. | 502/117 |
|---|---|---|---|
| 5,965,759 A * | 10/1999 | Lin | 556/11 |
| 6,177,376 B1 | 1/2001 | Fritze et al. | 502/110 |

FOREIGN PATENT DOCUMENTS

| EP | 819695 | 9/2003 |
|---|---|---|
| WO | 99/36427 | 7/1999 |
| WO | 00/17213 | 3/2000 |
| WO | 02/083699 | 10/2002 |
| WO | 03/057705 | 7/2003 |
| WO | WO 2004/099225 | 11/2004 |

OTHER PUBLICATIONS

Yoder et al. Organometallics, 1998, 17, 4946-4958.*
Luigi Resconi et al., "Selectivity in Propene Polymerization with Metallocene Catalysts," *Chem. Rev.*, vol. 100(4), p. 1253-1345 (2000).
J. Yoder et al., Racemic-Meso Interconversion for *ansa*-Scandocene and *ansa*-Yttrocene Derivatives. Molecular Structures of rac-$\{Me_2Si[n^5-C_5H_2-2, 4-(CHMe_2)_2]_2\}ScCl\cdot LiCl(THF)_2$, [*meso*-$\{Me_2Si[n^5-C_5H_2-2,4-(CHMe_2)_2]_2\}Y(\mu_2-Cl)]_2$, and *meso*-$\{Me_2Si[n^5-C_5H_2, 4-(CHMe_2)_2]_2\}Zr(NMe_2)_2$, *Organometallics*, vol. 17(23), p. 4946-4958 (1998).

* cited by examiner

*Primary Examiner*—Ling-Siu Choi
(74) *Attorney, Agent, or Firm*—Jarrod N. Raphael

(57) ABSTRACT

An isomerization process comprising the step of contacting a slurry or a solution comprising the meso or meso-like form of one or more bridged metallocene compounds of group 4 of the Periodic Table of the Elements having $C_2$ or $C_2$-like symmetry with an isomerization catalyst of formula (I) $[R_4W]^+X^-$ (I) wherein: W is a nitrogen or a phosphorus atom; R, equal to or different from each other, are $C_1$-$C_{40}$ hydrocarbon radicals and $X^-$ is an halide atom.

13 Claims, No Drawings

PROCESS FOR THE ISOMERIZATION OF METALLOCENE COMPOUNDS

The present invention relates to a process for the conversion of the meso or meso-like form of a metallocene compound to the corresponding racemic or racemic-like form. The meso or the meso-like form to be subjected to the process of the invention can be admixed with the corresponding racemic (rac) or racemic-like form.

Metallocene compounds are well known complexes, mainly used as catalyst components for the polymerization of olefins. Processes for the synthesis of such metallocene compounds tend to produce mixtures of racemic and meso form. Usually the racemic form produces stereoregular polymers while the meso form is inactive or produces low molecular weight atactic polymers. The racemic form is therefore the most used as polymerization catalyst component. Consequently it is desirable to obtain from the synthesis the racemic (rac) form or a mixture where the racemic form is predominant in order to reduce the work for the physical separation of the two isomers.

EP 819 695 describes a process for the modification of the rac/meso ratio of a rac/meso mixture of a stereorigid bridged metallocene compounds by subjecting the mixture to a selective decomposition in the presence of compounds having either acidic hydrogen atoms or reactive halogen atoms, such as water, methanol, chlorotrimethylsilane. With this process, one isomeric form is decomposed with a consequently lowering of the overall yield of the process.

WO 00/017213 describes an isomerization process in which the meso form or a mixture of racemic and meso form of a bridged metallocene compound is contacted with a Group 1 and/or 2 metal halide isomerization catalyst in a liquid medium. This process has the drawback that the elimination of the metal halide from the reaction mixture could be complicated.

Organometallics 1998, 17, 1946-4958 describes a series of reactions in which rac-dimethylsilyl(1,3-diisopropylcyclopentadienyl)scandium allyl is isomerized to a rac/meso mixtures by using different isomerization catalysts. Among all $(n-C_7H_{15})_4NCl$ and $(n-C_7H_{15})_4NBr$ are used. This isomerization reaction is obviously not useful for an industrial process which target is to obtain the rac isomer. Moreover, on page 4953 of this document it is stated that the isomerization is discouraged for metallocenes of group 4, thus creating a prejudice in using this kind of reaction with metallocene compounds in which the central metal belongs to group 4 of the periodic table of the elements.

Thus it is desirable to find an alternative isomerization process that allows isomerizing the meso or meso-like form of a bridged metallocene compounds in the rac or rac-like form in an easy way.

An object of the present invention is an isomerization process comprising the step of contacting a slurry or a solution comprising the meso or meso-like form of one or more bridged metallocene compounds of group 4 of the Periodic Table of the Elements having $C_2$ or $C_2$-like symmetry with an isomerization catalyst of formula (I)

$$[R_4W]^+X^- \qquad (I)$$

wherein:

W is a nitrogen or a phosphorus atom; preferably W is nitrogen;

R, equal to or different from each other, are $C_1$-$C_{40}$ hydrocarbon radicals optionally containing one or more heteroatoms belonging to groups 13-17 of the Periodic Table of the Elements; two R can also join to form a saturated or unsaturated $C_5$-$C_6$ membered cycle containing the atom W to form for example a pyrrollyl, a pirrolydinyl or a pyperidinyl radical or two R can also join to form a radical of formula (II)

wherein $R^1$, equal to or different from each other, are $C_1$-$C_{20}$ hydrocarbon radicals optionally containing one or more heteroatoms belonging to groups 13-17 of the Periodic Table of the Elements; preferably $R^1$ are linear or branched, cyclic or acyclic, $C_1$-$C_{12}$-alkyl, $C_2$-$C_{12}$ alkenyl, $C_2$-$C_{12}$ alkyl, $C_6$-$C_{12}$-aryl, $C_7$-$C_{12}$-alkylaryl or $C_7$-$C_{12}$-arylalkyl radicals; P is a phosphorous atom bonded with a double bond to the atom W; preferably R are linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals, optionally containing one or more heteroatoms belonging to groups 13-17 of the Periodic Table of the Elements;

more preferably R is a $C_1$-$C_{40}$-alkyl, $C_6$-$C_{40}$-aryl or $C_7$-$C_{40}$-alkylaryl radical, such as n-butyl, n-hexyl, phenyl and benzyl (Bz) radicals; and $X^-$ is an halide atom such as $Cl^-$, $Br^-$, $I^-$, $F^-$, preferably $X^-$ is chloride ($Cl^-$) or bromide ($Br^-$).

Examples of compounds of formula (I) are $(CH_3(CH_2)_3)_4NBr$, $(CH_3(CH_2)_5)_4NBr$, $(CH_3CH_2)_3(C_6H_5CH_2)NBr$, $(CH_3(CH_2)_3)_4NCl$, $(CH_3CH_2)_3(C_6H_5CH_2)NCl$, $(CH_3(CH_2)_3)_4PBr$, $(CH_3(CH_2)_5)_4PBr$, $(CH_3CH_2)_3(C_6H_5CH_2)PBr$, $(CH_3(CH_2)_3)_4PCl$,

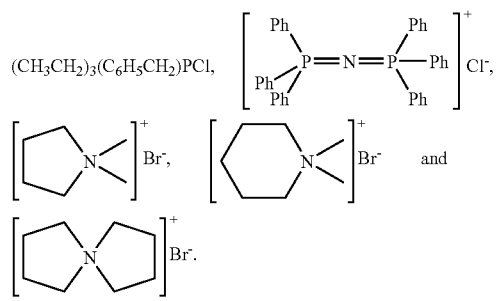

The bridged metallocene compounds of group 4 of the Periodic Table of the Elements having $C_2$ or $C_2$-like symmetry have two bridged cyclopentadienyl moieties linked to the central metal atom trough a Π bond. The central metal atom is zirconium, titanium or hafnium, preferably zirconium.

For the purpose of the present invention, the term "$C_2$ symmetry" means that in the metallocene compound two isomeric forms are possible, the racemic and the meso forms. These isomeric forms are well known in the art for example they are cited in *Chem. Rev.* 2000, 100, 1253-1345.

For the purpose of the present invention, the term "$C_2$-like symmetry" means that in the metallocene compound two isomeric forms are possible, the racemic-like and the meso-like form.

"Racemic-like form" means that the bulkier substituents of the two cyclopentadienyl moieties on the metallocene compound are on the opposite sides with respect to the plane containing the zirconium and the centre of the cyclopentadienyl moieties as shown in the following-compound;

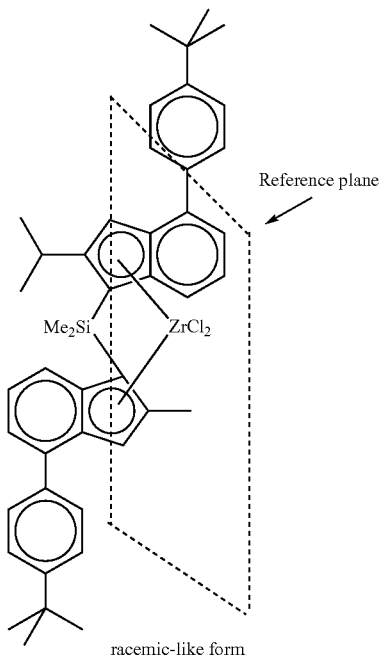

racemic-like form

Conversely meso-like form means that the bulkier substituents of the two cyclopentadienyl moieties on the metallocene compound are on the same side with respect to the plane containing the zirconium and the centre of the cyclopentadienyl moieties as shown in the following compound.

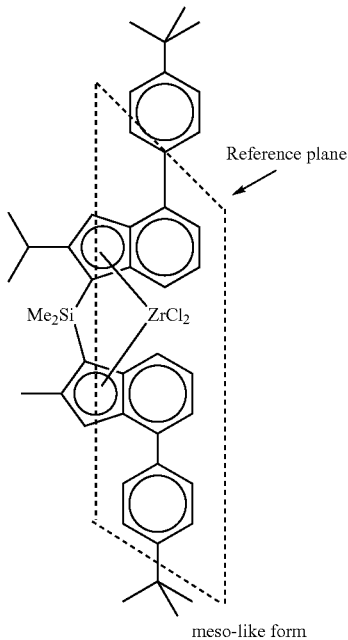

meso-like form

With the process of the present invention the meso or meso-like form of one or more bridged metallocene compounds of group 4 of the Periodic Table of the Elements having $C_2$ or $C_2$-like symmetry can be used alone or in a mixture comprising the racemic or racemic-like form.

According to a preferred embodiment, the process of the present invention is carried out in an aprotic solvent, either polar or apolar. Said aprotic solvent can be an aromatic or aliphatic hydrocarbon, optionally halogenated or optionally containing heteroatoms belonging to the group 16 of the periodic table, or an ether. Preferably it is selected from the group consisting of benzene, toluene, pentane, hexane, heptane, cyclohexane, dichloromethane, chlorobenzene, diethylether, tetrahydrofuran, 1,2 dimethoxyethane N,N-dimethylformamide, dimethyl sulfoxide or mixtures thereof. Preferably the process of the present invention is carried out in the presence of one or more ethers such as tetrahydrofuran or 1,2 dimethoxyethane; more preferably the solvent contains at least 5% by volume of one or more ethers.

The process of the present invention can be carried out at a temperature ranging from 0° C. to a temperature below the temperature of decomposition of the bridged metallocene compound in the selected solvent, usually up to 180° C. Preferably the process of the present invention is carried out at a temperature ranging from 10° C. to 150° C., more preferably from 30° C. to 90° C., even more preferably from 40° C. to 90° C.

The reaction time depends on the temperature, on the wished degree of isomerization, on the metallocene to be used. Generally it ranges from 0.1 hour to 65 hours, preferably from 1 hour to 24 hours. The skilled in the art can easily select the reaction time in view of the results to be obtained.

The process of the present invention can be advantageously carried out in an inert atmosphere, i.e. in the absence of oxygen, water or any other compounds able to decompose the metallocene.

The molar ratio between the isomerization catalyst and the metal of the bridged metallocene compound is preferably comprised between 0.01 to 300; more preferably the ratio is from 0.01 to 100, even more preferably from 0.1 to 10; particularly preferred ratio range is from 0.2 to 5.

With the process of the present invention it is possible to convert at least part of the meso or meso-like form to the racemic or racemic-like form of a bridged metallocene compound. This allows to improve the final yield in term of the racemic or racemic-like isomer of the whole process for synthesising the target metallocene compound. The removal of the isomerization catalyst and the final purification of the racemic or racemic like isomer can be carried out according to the procedure commonly used in the art.

The process of the present invention can be used as such or it can be part of a one-pot process for obtaining metallocene compounds starting from the ligands, such as the processes described in EP 03101268.5; WO 03/057705; WO 99/36427 and WO 02/083699.

Bridged metallocene compounds having $C_2$ symmetry or $C_2$-like symmetry that can be used in the process of the present invention are preferably compounds of formula (III)

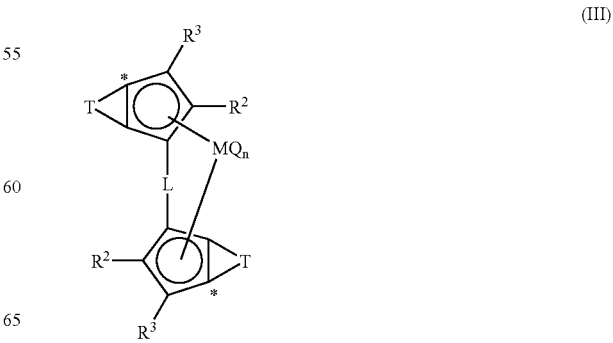

(III)

wherein:

M is a transition metal belonging to group 4, preferably M is zirconium, or hafnium; the substituents Q, equal to or different from each other, are monoanionic sigma ligands selected from the group consisting of hydrogen, halogen, $R^8$, $OR^8$, $OCOR^8$, $SR^8$, $NR^8_2$ and $PR^8_2$, wherein $R^8$ is a linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radical optionally containing one or more Si or Ge atoms;

or two Q can optionally form a substituted or unsubstituted butadienyl radical or a OR'O group wherein R' is a divalent radical selected from $C_1$-$C_{20}$ akylidene, $C_6$-$C_{40}$ arylidene, $C_7$-$C_{40}$ alkylarylidene and $C_7$-$C_{40}$ arylalkylidene radicals;

the substituents Q are preferably the same and are preferably halogen atoms, $R^8$, $OR^8$ and $NR^8_2$; wherein $R^8$ is preferably a $C_1$-$C_{10}$ alkyl, $C_6$-$C_{20}$ aryl or $C_7$-$C_{20}$ arylalkyl group, optionally containing one or more Si or Ge atoms; more preferably, the substituents Q are selected from the group consisting of —Cl, -Br, -Me, -Et, -n-Bu, -sec-Bu, -Ph, -Bz, —$CH_2SiMe_3$, —OEt, —OPr, —OBu, —OBz and —$NMe_2$;

n is an integer equal to the oxidation state of the metal M minus 2;

L is a divalent bridging group selected from $C_1$-$C_{20}$ alkylidene, $C_3$-$C_{20}$ cycloalkylidene, $C_6$-$C_{20}$ arylidene, $C_7$-$C_{20}$ alkylarylidene, or $C_7$-$C_{20}$ arylalkylidene radicals optionally containing heteroatoms belonging to groups 13-17 of the Periodic Table of the Elements, and silylidene radical containing up to 5 silicon atoms such as $SiMe_2$, $SiPh_2$; preferably L is a divalent group $(ZR^9_m)_q$; Z being C, Si, Ge, N or P, and the $R^9$ groups, equal to or different from each other, being hydrogen or a linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radical or two $R^9$ can form a aliphatic or aromatic $C_4$-$C_7$ ring; preferably $R^9$ is a hydrogen atom or a methyl or phenyl radical; preferably Z is Si or C;

m is 1 or 2, and more specifically it is 1 when Z is N or P, and it is 2 when Z is C, Si or Ge; q is an integer ranging from 1 to 4; preferably q is 1 or 2;

more preferably L is selected from $Si(CH_3)_2$, $SiPh_2$, SiPhMe, $SiMe(SiMe_3)$, $CH_2$, $(CH_2)_2$, $(CH_2)_3$ or $C(CH_3)_2$;

$R^2$, $R^3$, equal to or different from each other, are hydrogen atoms, halogen atoms or linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radicals, optionally containing one or more heteroatoms belonging to groups 13-17 of the Periodic Table of the Elements;

T, equal to or different from each other, is a moiety of formula (IIIa) or (IIIb):

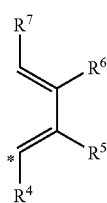

(IIIa)

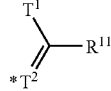

(IIIb)

wherein:
the atom marked with the symbol * bonds the atom marked with the same symbol in the compound of formula (III);
$T^1$ is a sulphur atom, a oxygen atom or a $CR^{10}_2$ or a $NR^{12}$ group, wherein $R^{10}$, equal to or different from each other, are hydrogen atoms, halogen atoms or linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radicals, optionally containing one or more heteroatoms belonging to groups 13-17 of the Periodic Table of the Elements; and $R^{12}$ is a or linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radical, optionally containing one or more heteroatoms belonging to groups 13-17 of the Periodic Table of the Elements; preferably $T^1$ is sulphur.

$T^2$ is a $CR^{10}$ group or a nitrogen atom; wherein $R^{10}$ is a hydrogen atom, a halogen atom or linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radical, optionally containing one or more heteroatoms belonging to groups 13-17 of the Periodic Table of the Elements; preferably $T^2$ is a $CR^{10}$ group;
with the proviso that if $T^2$ is a nitrogen atom $T^1$ is $CR^{10}_2$;

$R^4$, $R^5$, $R^6$, $R^7$, and $R^{11}$, equal to or different from each other, are hydrogen atoms, halogen atoms or linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radicals, optionally containing one or more heteroatoms belonging to groups 13-17 of the Periodic Table of the Elements; or two adjacent $R^4$, $R^5$, $R^6$, $R^7$, $R^{10}$ and $R^{11}$ form one or more 3-7 membered ring optional containing heteroatoms belonging to groups 13-17 of the periodic table;
preferably $R^2$ and $R^{11}$, equal to or different from each other, are linear or branched $C_1$-$C_{20}$-alkyl radicals, such as methyl, ethyl or isopropyl radicals;
preferably $R^4$ and $R^{10}$, equal to or different from each other, are hydrogen atoms in $C_6$-$C_{20}$-aryl, or $C_7$-$C_{20}$-arylalkyl radicals such as phenyl, 4-tert-butyl phenyl radicals.

Non limiting examples of compounds belonging to formula (I) are the following compounds;
dimethylsilanediylbis(indenyl)zirconium dichloride, dimethylsilanediylbis(2-methyl-4-phenylindenyl)zirconium dichloride,
dimethylsilanediylbis(4-naphthylindenyl)zirconium dichloride,
dimethylsilanediylbis(2-methylindenyl)zirconium dichloride,
dimethylsilanediylbis(2-methyl-4-t-butylindenyl)zirconium dichloride,
dimethylsilanediylbis(2-methyl-4-isopropylindenyl)zirconium dichloride,
dimethylsilanediylbis(2,4-dimethylindenyl)zirconium dichloride,
dimethylsilanediylbis(2-methyl-4,5-benzoindenyl)zirconium dichloride,
dimethylsilanediylbis(2,4,7-trimethylindenyl)zirconium dichloride, dimethylsilanediylbis(2,4,6-trimethylindenyl)zirconium dichloride,
dimethylsilanediylbis(2,5,6-trimethylindenyl)zirconium dichloride,
methyl(phenyl)silanediylbis(2-methyl-4,6-diisopropylindenyl)-zirconium dichloride,
methyl(phenyl)silanediylbis(2-methyl-4-isopropylindenyl)-zirconium dichloride,
1,2-ethylenebis(indenyl)zirconium dichloride,
1,2-ethylenebis(4,7-dimethylindenyl)zirconium dichloride,
1,2-ethylenebis(2-methyl-4-phenylindenyl)zirconium dichloride,
1,4-butanediylbis(2-methyl-4-phenylindenyl)zirconium dichloride,
1,2-ethylenebis(2-methyl-4,6-diisopropylindenyl)zirconium dichloride,
1,4-butanediylbis(2-methyl-4-isopropylindenyl)zirconium dichloride,
1,4-butanediylbis(2-methyl-4,5-benzoindenyl)zirconium dichloride,
1,2-ethylenebis(2-methyl-4,5-benzoindenyl)zirconium dichloride,
dimethylsilanediylbis-6-(3-methylcyclopentadienyl-[1,2-b]-thiophene) dichloride;
dimethylsilanediylbis-6-(4-methylcyclopentadienyl-[1,2-b]thiophene)zirconium dichloride;
dimethylsilanediylbis-6-(4-isopropylcyclopentadienyl-[1,2-b]-thiophene)zirconium dichloride;
dimethylsilanediylbis-6-(4-ter-butylcyclopentadienyl-[1,2-b]-thiophene)zirconium dichloride;
dimethylsilanediylbis-6-(3-isopropylcyclopentadienyl-[1,2-b]-thiophene)zirconium dichloride;
dimethylsilanediylbis-6-(3-phenylcyclopentadienyl-[1,2-b]-thiophene)zirconium dichloride;
dimethylsilanediylbis-6-(2,5-dichloride-3-phenylcyclopentadienyl-[1,2-b]-thiophene]zirconium dimethyl;
dimethylsilanediylbis-6-[2,5-dichloride-3-(2-methylphenyl)cyclopentadienyl-[1,2-b]-thiophene]zirconium dichloride;
dimethylsilanediylbis-6-[2,5-dichloride-3-(2,4,6-trimethylphenyl)cyclopentadienyl-[1,2-b]-thiophene]zirconium dichloride;
dimethylsilanediylbis-6-[2,5-dichloride-3-mesitylenecyclopentadienyl-[1,2-b]-thiophene]zirconium dichloride;
dimethylsilanediylbis-6-(2,4,5-trimethyl-3-phenylcyclopentadienyl-[1,2-b]-thiophene)zirconium dichloride;
dimethylsilanediylbis-6-(2,5-diethyl-3-phenylcyclopentadienyl-[1,2-b]-thiophene)zirconium dichloride;
dimethylsilanediylbis-6-(2,5-diisopropyl-3-phenylcyclopentadienyl-[1,2-b]-thiophene)zirconium dichloride;
dimethylsilanediylbis-6-(2,5-diethyl-butyl-3-phenylcyclopentadienyl-[1,2-b]-thiophene)zirconium dichloride;
dimethylsilanediylbis-6-(2,5-ditrimethylsilyl-3-phenylcyclopentadienyl-[1,2-b)-thiophene)zirconium dichloride;
dimethylsilanediylbis-6-(3-methylcyclopentadienyl-[1,2-b]-silole)zirconium dichloride;
dimethylsilanediylbis-6-(3-isopropylcyclopentadienyl-[1,2-b]-silole) zirconium dichloride;
dimethylsilanediylbis-6-(3-phenylcyclopentadienyl-[1,2-b]-silole) zirconium dichloride;
dimethylsilanediylbis-6-(2,5-dichloride-3-phenylcyclopentadienyl-[1,2-b]-silole)zirconium dichloride;
dimethylsilanediylbis-6-[2,5-dichloride-3-(2-methylphenyl)cyclopentadienyl-[1,2-b]-silole]zirconium dichloride;
dimethylsilanediylbis-6-[2,5-dichloride-3-(2,4,6-trimethylphenyl)cyclopentadienyl-[1,2-b]-silole]zirconium dichloride;
dimethylsilanediylbis-6-[2,5-dichloride-3-mesitylenecyclopentadienyl-[1,2-b]-silole]zirconium dichloride;
dimethylsilanediylbis-6-(2,4,5-trimethyl-3-phenylcyclopentadienyl-[1,2-b]-silole)zirconium dichloride;
Dimethylsilanediylbis(2-methyl-4-p-tert-butylphenylindenyl)zirconium dichloride;
Dimethylsilanediyl(2-isopropyl-4-p-tert-butylphenylindenyl)(2-methyl-4-p-tert-butylphenylindenyl)zirconium dichloride;
Dimethylsilanediyl(2-isopropyl-4-p-tert-butylphenylindenyl)(2-methyl-4-p-tert-butyl-7-methylphenylindenyl)zirconium dichloride;
as well as the corresponding zirconium dimethyl, hydrochloro dihydro and $\eta^4$-butadiene compounds.

The following examples are given to illustrate and not to limit the invention.

EXAMPLES

Dimethylsilanediyl [2-methyl-4-(4'-tert-butylphenyl)indenyl][2-isopropyl-4-(4'-tert-butylphenyl)indenyl)] dimethyl zirconium (A) is prepared following the same procedure described in example 5 of PCT/EP02/14899 by using [2-methyl-4-(4'-tert-butylphenyl)indenyl] [2-isopropyl-4(4'-tert-butylphenyl)indenyl)]dimethylsilane instead of bis(2-methyl-indenyl)dimethylsilane.

Dimethylsilanediylbis[2-methyl-4,5-benzo-1-indenyl] dimethyl zirconium (B) was prepared according to U.S. Pat. No. 6,177,376.

Dimethylsilanediylbis[2-methyl-4,5-benzo-1-indenyl] zirconium dichloride (C) was prepared according to U.S. Pat. No. 5,830,821.

Examples 1-7

General Procedure

A purified meso enriched metallocene was dissolved (or slurried) at room temperature under nitrogen in the solvent indicated in table 1. The isomerization catalyst specified in table 1 was added and then the mixture was heated for few hours. NMR analysis of a sample of the resulting solution (or slurry) showed that the rac/meso ratio of the metallocene was substantially improved in favour of the rac isomer. The latter was also isolated in higher yields compared with the yields achieved by using standard procedures. The rac/meso ratios were determined by NMR analysis. The proton spectra of metallocenes were obtained on a Bruker DPX 200 spectrometer operating in the Fourier transform mode at room temperature at 200.13 MHz. The samples were dissolved in $CD_2Cl_2$ (Aldrich, 99.8 atom % D); preparation of the samples was carried out under nitrogen using standard inert atmosphere techniques. The residual peak of $CHDCl_2$ in the $^1H$ spectra (5.35 ppm) was used as a reference. Proton spectra were acquired with a 15° pulse and 2 seconds of delay between pulses; 32 transients were stored for each spectrum.

TABLE 1

| Ex. | Met. | starting rac/meso ratio | Isomerization catalyst (n° eq./Zr) | Solvent | T (° C.) | t (h) | final rac/meso ratio |
|---|---|---|---|---|---|---|---|
| 1 | A | 2.4/97.6 | n-Bu$_4$NBr (0.22/1) | THF | 65 | 5 | 94.0/6.0 |
| 2 | A | 31.7/68.3 | n-Bu$_4$NBr (0.21/1) | toluene, THF 1/1.7 v/v | 80 | 4 | 78.9/21.1 |
| 3 | A | 31.7/68.3 | [CH$_3$(CH$_2$)$_5$]$_4$NBr (0.23/1) | toluene, THF 1/1.7 v/v | 80 | 10 | 76.5/23.5 |
| 4 | A | 31.7/68.3 | (CH$_3$CH$_2$)$_3$BzNCl (0.23/1) | toluene, THF 1/1.7 v/v | 80 | 4 | 75.2/24.8 |
| 5 | B | 26.8/73.2 | n-Bu$_4$NBr (0.22/1) | THF | 65 | 2 | 71.9/28.1 |
| 6 | C | 17.7/82.3 | n-Bu$_4$NBr (0.23/1) | THF | 65 | 2.5 | 94.4/5.6 |
| 7 | A | 33.3/66.7 | n-Bu$_4$NBr (0.21/1) | chlorobenzene | 80 | 7.5 | 70.4/29.6 |
| 8 | A | 33.3/66.7 | Et$_3$BzNCl (0.21/1) | toluene | 80 | 3 | 61.5/38.5 | note:
no remarkable amount of decomposition was observed.
Et = ethyl radical
n-Bu = normal butyl radical;
Bz = benzil radical Comparative Example 1

A sample of ammonium chloride (Aldrich, MW 53.49) was dried at 125° C. for 8 h under vacuum. An aliquot of this sample (Aldrich, 17.0 mg, 0.32 mmol, NH$_4$Cl/dimethyl complex=0.20/1) was added at room temperature under nitrogen atmosphere to a solution of 1.16 g of dimethylsilanediyl[2-methyl-4-(4'-tert-butylphenyl)indenyl][2-isopropyl-4-(4'-tertbutylphenyl)indenyl)] dimethyl zirconium (rac/meso 31.7/68.3, MW=728.26, 1.59 mmol) in 25 mL of THF and 15 mL of toluene in a 50 mL Schlenk flask. At the end of the addition, the reaction mixture was heated at 80° C. for 2.5 h and followed by NMR analysis: the rac/meso ratio resulted to be 34/66 and a small amount of decomposition to the ligand was also observed. Additional ammonium chloride (100.0 mg, 1.87 mmol, total NH$_4$Cl/dimethyl complex=1.38/1) was added at room temperature and then the resulting mixture was heated at 80° C. for 3.5 h. Different aliquots of the mixture were taken, dried and analysed by $^1$H NMR in CD$_2$Cl$_2$. The final rac/meso ratio resulted to be 45/55 and a remarkable amount of decomposition to the ligand (ca. 20% mol. calculated by NMR) was also observed.

Comparative Example 2

A sample of triethylammine hydrochloride (Aldrich, 98%, MW 137.65, 25.7 mg, 0.18 mmol, NHEt$_3$Cl/dimethyl complex=0.22/1) was suspended at room temperature into 5 mL of THF and added under nitrogen atmosphere to a suspension of 0.58 g of dimethylsilanediyl[2-methyl-4-(4'-tert-butylphenyl)indenyl][2-isopropyl-4-(4'-tertbutylphenyl)indenyl)] dimethyl zirconium (rac/meso 30/70, MW=728.26, 0.80 mmol) in 15 mL of THF in a 50 mL Schlenk flask. At the end of the addition, the reaction mixture was heated at reflux for 2 h and followed by NMR analysis: the rac/meso ratio resulted to be 45/55, but a remarkable amount of decomposition was also observed. The heating was then continued for additional 2 h, but no change in the rac/meso ratio was observed by NMR analysis.

The invention claimed is:
1. An isomerization process comprising:
contacting a slurry or a solution comprising a meso or meso-like form of at least one bridged metallocene compound of group 4 of the Periodic Table of the Elements having C$_2$ or C$_2$-like symmetry with an isomerization catalyst of formula (I):

[R$_4$W]$^+$X$^-$     (I)

wherein W is nitrogen or phosphorus;
R, equal to or different from each other, are C$_1$-C$_{40}$ hydrocarbon radicals optionally containing one or more heteroatoms belonging to groups 13-17 of the Periodic Table of the Elements; two R can optionally join to form a saturated or unsaturated C$_5$-C$_6$ membered cycle containing W or two R can optionally join to form a radical of formula (II):

wherein R$^1$, equal to or different from each other, are C$_1$-C$_{20}$ hydrocarbon radicals optionally containing one or more heteroatoms belonging to groups 13-17 of the Periodic Table of the Elements; P is phosphorous bonded with a double bond to W; and
X$^-$ is a halide.

2. The isomerization process according to claim 1, wherein the slurry or solution comprises a mixture comprising the mesa or mesa-like form of at least one bridged metallocene compound of group 4 of the Periodic Table of the Elements having C$_2$ or C$_2$-like symmetry, and a racemic or racemic-like form of at least one bridged metallocene compound of group 4 of the Periodic Table of the Elements having C$_2$ or C$_2$-like symmetry.

3. The isomerization process according to claim 1, wherein R are linear or branched, cyclic or acyclic, C$_1$-C$_{40}$-alkyl, C$_2$-C$_{40}$ alkenyl, C$_2$-C$_{40}$ alkynyl, C$_6$-C$_{40}$-aryl, C$_7$-C$_{40}$-alkylaryl or C$_7$-C$_{40}$-arylalkyl radicals, optionally containing one or more heteroatoms belonging to groups 13-17 of the Periodic Table of the Elements; two R can optionally join to form a saturated or unsaturated C$_5$-C$_6$ membered cycle containing W; and X$^{31}$ is chloride or bromide.

4. The isomerization process according to claim 1, wherein W is nitrogen.

5. The isomerization process according to claim 1, wherein the isomerization process is carried out in an aprotic solvent.

6. The isomerization process according to claim 5, wherein the aprotic solvent is polar or apolar.

7. The isomerization process according to claim 5, wherein the aprotic solvent is an optionally halogenated aromatic or aliphatic hydrocarbon, optionally containing heteroatoms belonging to the group 16 of the Periodic Table of the Elements.

8. The isomerization process according to claim 5, wherein the aprotic solvent is an ether.

9. The isomerization process according to claim 1, wherein the isomerization process is carried out in presence of one or more ethers.

10. The isomerization process according to claim 1, wherein the isomerization process is carried out at a temperature ranging from 0 to a temperature below a temperature of decomposition of the bridged metallocene compound.

11. The isomerization process according to claim 1, wherein the bridged metallocene compound having $C_2$ symmetry or $C_2$-like symmetry has formula (III)

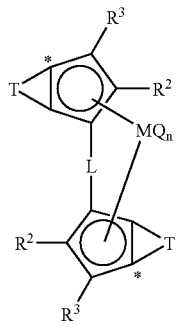

(III)

wherein M is a transition metal belonging to group 4;
Q, equal to or different from each other, are monoanionic sigma ligands selected from the group consisting of hydrogen, halogen, $R^8$, $OR^8$, $OCOR^8$, $SR^8$, $NR^8_2$, and $PR^8_2$, wherein $R^8$ is a linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radical optionally containing one or more Si or Ge atoms; or two Q can optionally form a substituted or unsubstituted butadienyl radical or OR'O, wherein R' is a divalent radical selected from $C_1$-$C_{20}$ alkylidene, $C_6$-$C_{40}$ arylidene, $C_7$-$C_{40}$ alkylarylidene and $C_7$-$C_{40}$ arylalkylidene radicals;
n is an integer equal to an oxidation state of M minus 2;
L is a divalent bridging group selected from a $C_1$-$C_{20}$ alkylidene, a $C_3$-$C_{20}$ cycloalkylidene, a $C_6$-$C_{20}$ arylidene, a $C_7$-$C_{20}$ alkylarylidene, or a $C_7$-$C_{20}$ arylalkylidene radical optionally containing heteroatoms belonging to groups 13-17 of the Periodic Table of the Elements, and a silylidene radical containing up to 5 silicon atoms;
$R^2$ and $R^3$, equal to or different from each other, are hydrogen, halogen, or linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radicals, optionally containing one or more heteroatoms belonging to groups 13-17 of the Periodic Table of the Elements;
T, equal to or different from each other, is a moiety of formula (IIIa) or (IIIb):

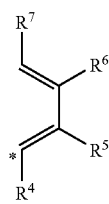

(IIIa)

-continued

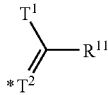

(IIIb)

wherein the atom marked with symbol * bonds to the atom marked with the same symbol in the bridged metallocene compound;
$T^1$ is sulphur, oxygen, or $CR^{10}_2$, or $NR^{12}$, wherein $R^{10}$, equal to or different from each other, are hydrogen, halogen, or are linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radicals, optionally containing one or more heteroatoms belonging to groups 13-17 of the Periodic Table of the Elements; and $R^{12}$ is a or linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radical, optionally containing one or more heteroatoms belonging to groups 13-17 of the Periodic Table of the Elements;
$T^2$ is $CR^{12}$ or nitrogen, wherein $R^{10}$ is hydrogen, halogen, or a linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radical, optionally containing one or more heteroatoms belonging to groups 13-17 of the Periodic Table of the Elements, with the proviso that if $T^2$ is nitrogen, $T^1$ is $CR^{10}_2$;
$R^4$, $R^5$, $R^6$, $R^7$, and $R^{11}$, equal to or different from each other, are hydrogen, halogen, or linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radicals, optionally containing one or more heteroatoms belonging to groups 13-17 of the Periodic Table of the Elements; or two adjacent $R^4$, $R^5$, $R^6$, $R^7$, $R^{10}$ and $R^{11}$ form at least one 3-7 membered ring optional containing heteroatoms belonging to groups 13-17 of the periodic table.

12. The isomerization process according to claim 11, wherein M is zirconium, or hafnium;
Q are equal and are halogens, $R^8$, $OR^8$, or $NR^8_2$, wherein $R^8$ is preferably a $C_1$-$C_{10}$ alkyl, $C_6$-$C_{20}$ aryl or $C_7$-$C_{20}$ arylalkyl group, optionally containing one or more Si or Ge atoms;
L is a divalent group $(ZR^9_m)q$;
Z is C, Si, Ge, N or P; and
$R^9$, equal to or different from each other, are hydrogen or a linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radicals, or two $R^9$ can optionally form an aliphatic or aromatic $C_4$-$C_7$ ring.

13. The isomerization process according to claim 11, wherein $R^2$ and $R^{11}$, equal to or different from each other, are linear or branched $C_1$-$C_{20}$-alkyl radicals;
$R^4$ and $R^{10}$, equal to or different from each other, are hydrogen or $C_6$-$C_{20}$-aryl, or $C_7$-$C_{20}$-arylalkyl radicals;
$T^1$ is sulphur; and
$T^2$ is a $CR^{10}$ group.

* * * * *